United States Patent [19]

White et al.

[11] 4,263,404

[45] Apr. 21, 1981

[54] RIFAMYCIN R AND MICROORGANISMS USEFUL IN THE PRODUCTION OF RIFAMYCINS

[75] Inventors: Richard J. White, High Wycombe, England; Giancarlo Lancini, Pavia; Piero Antonini, Arluno, both of Italy

[73] Assignee: Gruppo Lepetit S.p.A., Milan, Italy

[21] Appl. No.: 745,932

[22] Filed: Nov. 29, 1976

[30] Foreign Application Priority Data

Aug. 30, 1974 [GB] United Kingdom .............. 37913/74

Related U.S. Application Data

[62] Division of Ser. No. 601,559, Aug. 4, 1976, Pat. No. 4,042,683.

[51] Int. Cl.³ .................. C07D 491/06; A61K 35/74; C12N 1/20; A61K 31/395

[52] U.S. Cl. .................................... 435/253; 435/119; 435/872; 435/886; 260/239.3 P; 424/117; 424/115; 424/120; 424/121

[58] Field of Search .................. 260/239.3 P; 195/96; 435/119, 872, 886; 424/117, 115, 120, 121

[56] References Cited

U.S. PATENT DOCUMENTS 4,042,683  8/1977  White et al. .......................... 435/119

Primary Examiner—Robert T. Bond

[57] ABSTRACT

Novel rifamycin compounds, designated P, Q, R and U, produced by the fermentation of mutant strains of *Streptomyces mediterranei*.

4 Claims, No Drawings

RIFAMYCIN R AND MICROORGANISMS USEFUL IN THE PRODUCTION OF RIFAMYCINS

CROSS-REFERENCE TO RELATED APPLICATION

This is a division of application Ser. No. 601,559 filed Aug. 4, 1976 now U.S. Pat. No. 4,042,683.

This invention is directed to novel rifamycin compounds which are produced by fermentation of mutant strains of Streptomyces mediterranei in an aqueous nutrient medium under aerobic conditions. These novel rifamycins are hereinafter referred to as rifamycin P, rifamycin Q, rifamycin R and rifamycin U.

It has previously been reported that during fermentation in normal growth media, Streptomyces mediterranei synthesizes a family of antibiotics collectively referred to as the rifamycin complex (P. Sensi, et al., Antibiotics Annual 1959–1960, page 262). Subsequent work revealed that the addition of sodium diethyl barbiturate to the culture medium resulted essentially in the formation of a single fermentation product, rifamycin B (Margalith P. and Pagani H., Applied Microbiology, 9, 325, 1961). According to a further discovery, a mutant strain of Streptomyces mediterranei was found which elaborates essentially rifamycin B only, irrespective of the presence or absence of sodium diethyl barbiturate in the fermentation medium, so that an improved process for making rifamycin B results. The rifamycin B producing strain was identified as Streptomyces Mediterranei ATCC 21789. See U.S. Pat. No. 3,871,965.

The new antibiotic substances which are the object of this invention are produced by mutant strains derived from Streptomyces mediterranei ATCC 13685. The new strains are obtained by treating strain ATCC 13685 with common chemical mutagenic agents such as nitrous acid or nitroso guanidine derivatives or with physical mutagenic agents such as X rays and U.V. radiation. The new mutant strains rather than to the genus Streptomyces mediterranei are assigned to the genus Nocardia in accordance with the proposals by J. E. Thiemann et al., Arch. Mikrobiol., 67, 147–155 (1969).

ISOLATION OF THE MUTATED STRAINS PRODUCING NOVEL RIFAMYCINS

A suspension of spores of Streptomyces mediterranei ATCC 13685 was treated with N-methyl-N'-nitro-N-nitrosoguanidine at 1 mg/ml in a pH 9.0 tris(hydroxymethyl)aminomethane buffer for 60 minutes at 28° C. The mutagen-treated spores were then washed and plated onto Petri dishes containing Bennett agar. After 14 days incubation at 28° C., the surviving colonies were picked off and examined for their ability to inhibit the growth of Bacillus subtilis in the following manner: a disc of agar (diameter 4–8 mm) carrying a single colony was transferred onto a Petri dish containing Penassay agar at pH 7.2 previously seeded at 2% (v/v) with Bacillus subtilis.

Under these conditions rifamycin B is practically inactive and a normal colony producing rifamycin B gives no inhibition of the growth of Bacillus subtilis in the underlying agar, whereas any colony producing a novel rifamycin with antimicrobial activity will cause a clear cut zone of inhibition of growth around the disc of agar. Three strains were isolated in this way and were originally given our internal code D-2, MM18-6 and M-36. Samples of these microorganisms were deposited with the ATCC where they are identified respectively as Nocardia mediterranea ATCC 31064 Nocardia mediterranea ATCC 31065 and Nocardia mediterranea ATCC 31066.

DESCRIPTION OF THE NEW NOCARDIA MEDITERRANEA STRAINS

Table 1 reports the results of the macroscopic and mycroscopic examination of the Nocardia mediterranea strains identified respectively with the ATCC No. 31064, 31065 and 31066, and Table 2 reports the cultural characteristics of the same Nocardia mediterranea strains.

The characteristics of the parent strain Streptomyces mediterranei ATCC 13685 (ME/83) are also reported:

TABLE 1

| | Colonies | Aerial mycelium | Spores |
|---|---|---|---|
| N. mediterranea ATCC 31064 (D-2) | Colonies conical-crateriform and convolute, 2–3 mm. of diameter, reddish-brown with ochre yellow soluble pigment | Greyish to pinkish, branched, 0.6–0.8 μm of diameter | Cylindrical (0.8–1 μm × 3.0–5.0μ) |
| N. mediterranea ATCC 31065 (MM18-6) | Colonies conical-crateriform and convulate, 2–3 mm. of diameter, deep orange with deep orange-yellow soluble pigment | Pink to light orange branched, 0.6–0.8 μm of diameter | Cylindrical (0.8–μm × 3.0–5.0μ) |
| N. mediterranea ATCC 31066 (M-36) | Colonies conical-crateriform and convolate, 2–3 mm. of diameter, orange brown with amber soluble pigment | Pink to pink orange branched, 0.6–0.8 μm of diameter | Cylindrical (0.8–1 μm × 3.0–5.0μ) |
| Streptomyces mediterranei ATCC 13685 ME/83 | Colonies conical-crateriform and convolate, 2–3 mm of diameter, orange-yellow with light amber soluble pigment | Pinkish, branched, 0.6–0.8 μm of diameter | Cylindrical (0.8–1 μm × 3.0–5.0μ) |

TABLE 2

| Media | N. mediterranea ATCC 31064 (D-2) | N. mediterranea ATCC 31065 (MM 18-6) | N. mediterranea ATCC 31066 (M-36) | Streptomyces mediterranei ATCC 13685 (ME/83) |
|---|---|---|---|---|
| Oat meal agar | Abundant growth with slightly wrinkled surface, hazel-brown with orange edges. Pink-beige soluble pigment. | Abundant growth with smooth surface, orange. Traces of pinkish aerial mycelium. Some spores. Pink-beige soluble pigment. | Abundant with smooth surface, deep amber. Traces of pink aerial mycelium. Burnt amber soluble pigment. | Fair growth with smooth surface, yellowish with pinkish reverse. Whitish aerial mycelium with pink tinge. Traces of yellow- |

TABLE 2-continued

| Media | N. mediterranea ATCC 31064 (D-2) | N. mediterranea ATCC 31065 (MM 18-6) | N. mediterranea ATCC 31066 (M-36) | Streptomyces mediterranei ATCC 13685 (ME/83) |
|---|---|---|---|---|
| Yeast extract glucose agar (Medium No. 2 Shirling and Gottlieb) | Abundant growth with very wrinkled surface, amber. Greyish aerial mycelium, deep rusty soluble pigment. | Abundant growth with very wrinkled surface, brick red. Deep rusty soluble pigment. | Abundant growth with wrinkled surface. Vegetative mycelium, burnt amber. Burnt amber soluble pigment. | ish soluble pigment. Abundant growth with rough surface yellowish to pink. Scanty aerial mycelium. |
| Emerson's glucose agar | Abundant growth with very wrinkled and crusty surface, brick red Amber soluble pigment. | Abundant growth with very wrinkled and crusty surface, brick red, Amber soluble pigment. | Abundant growth with wrinkled surface, burnt amber. Burnt amber soluble pigment. | Abundant growth with rough surface, yellowish to pink orange. Pinkish aerial mycelium. Pale amber soluble pigment. |
| Bennett's agar | Abundant growth, very wrinkled, reddish brown Traces of greyish aerial mycelium. Ochre yellow soluble pigment. | Abundant growth with very wrinkled surface, deep orange. Deep yellow soluble pigment. | Abundant growth with wrinkled surface, orange brown. Amber soluble pigment. | Good growth, yellowish turning orange-yellow. Pinkish aerial mycelium Light amber soluble pigment. |
| Penassay agar | Moderate growth, slightly wrinkled light orange. No soluble pigment. | Moderate growth, slightly wrinkled light orange. No soluble pigment. | Moderate growth with smooth and thin surface, light orange. No soluble pigment. | Poor growth |
| Yeast extract molasse agar | Abundant growth very wrinkled, brick red Deep rusty soluble pigment. | Abundant growth with very wrinkled surface, brick red. Deep rusty soluble pigment. | Abundant growth with crusty surface, burnt amber Burnt amber soluble pigment. | Abundant growth with rough surface, colorless to yellowish. Whitish aerial mycelium. Deep amber soluble pigment. |
| Czapek-Dox saccharose agar | Moderate growth with smooth and thin surface light orange. Pale pink aerial mycelium. Some spores. Deep lemon yellow soluble pigment. | Good growth with smooth surface, orange. Light orange aerial mycelium | Abundant growth with smooth surface, salmon. Abundant aerial mycelium pink orange. Traces of light yellow soluble pigment. | Poor growth with thin surface, colorless to light melon. Traces of pinkish white aerial mycelium |
| Potato agar | Scarce growth,light orange. Light hazel brown soluble pigment. | No growth | Moderate growth with smooth surface. Light orange. No soluble pigment. | Poor growth with thin surface, colorless. Traces of whitish aerial mycelium. No soluble pigment. |
| Glucose asparagine agar | Abundant growth with smooth surface orange. Light yellow soluble pigment. | Scarce growth with smooth surface, light orange. No soluble pigment. | Fair growth, gold. No soluble pigment. | Fair growth with smooth and thin surface, light orange pink. Some light yellow soluble pigment. |
| Glycerol asparagine agar (medium n° 5 Shirling and Gottlieb) | Abundant growth with smooth surface deep orange. Traces of yellowish soluble pigment. | Scarce growth, deep orange. No soluble pigment. | Moderate growth with slightly wrinkled surface, deep orange. Traces of yellow soluble pigment. | Fair growth with smooth and thin surface. Light orange pink. Some light yellow soluble pigment. |
| Nutrient agar | Moderate growth with thin and smooth surface, pale orange. No soluble pigment. | Moderate growth with wrinkled and thin surface, pale orange. No soluble pigment. | Fair growth with thin and smooth surface, orange. No soluble pigment. | Moderate growth with smooth surface, melon to orange. Pinkish white aerial mycelium. |
| Pridham's agar | Moderate growth with smooth and thin surface, amber. Light pinkish-orange aerial mycelium. Pinkish soluble pigment. | Abundant growth with smooth surface, brick red. Pink aerial mycelium. Yellow soluble pigment. | Abundant growth, slightly crusty, amber brown. Traces of pinkish aerial mycelium. Amber brown soluble pigment. | Moderate growth with smooth surface, colorless with lobster red spots. Pink aerial mycelium. |
| Starch agar (medium n° 4 Shirling and Gottlieb) | Moderate growth with smooth surface orange. Abundant aerial mycelium, pink. Abundant production of spores. Yellow soluble pigment. Starch hydrolysis: negative. | Moderate growth with smooth surface, deep orange. Traces of straw soluble pigment. Starch hydrolysis: negative. | Abundant growth with smooth surface, orange. Traces of pinkish aerial mycelium. Light yellow soluble pigment. Starch hydrolysis: negative. | Poor growth, colorless to light orange pink. Scarce white aerial mycelium. Starch hydrolysis: doubtful. |
| Dextrose triptone agar | Abundant growth with wrinkled surface melon. Orange melon soluble pigment. | Moderate growth, wrinkled, orange. Orange yellow soluble pigment. | Abundant growth with wrinkled surface, rose-melon. Rose melon soluble pigment. | Abundant growth pink orange. Pinkish aerial mycelium. Light golden yellow soluble pigment. |
| Hickey's and Tresner's cobalt agar | Moderate growth with smooth and thin surface, colorless. Whitish aerial mycelium. Beige soluble pigment. | Abundant growth with smooth surface, rose melon. Light beige-rose soluble pigment. | Moderate growth with slightly wrinkled surface, rose-melon. Light beige soluble pigment. | Moderate growth, light pinkish orange. Some pinkish aerial mycelium. Yellowish soluble pigment. |
| Tyrosine agar | Abundant growth, very wrinkled and crusty | Abundant growth, very wrinkled and crusty. | Abundant growth with crusty surface, deep | Poor growth |

TABLE 2-continued

| Media | N. mediterranea ATCC 31064 (D-2) | N. mediterranea ATCC 31065 (MM 18-6) | N. mediterranea ATCC 31066 (M-36) | Streptomyces mediterranei ATCC 13685 (ME/83) |
| --- | --- | --- | --- | --- |
| (Medium n° 7 Shirling and Gottlieb) | brick red. Deep yellow soluble pigment. Tyrosine reaction: positive (good). | Deep orange. Pinkish-tan soluble pigment. Tyrosine reaction: strongly positive. | burnt orange. Yellow ochre soluble pigment. Tyrosine reaction: strongly positive. | |
| Ca-malate agar | Scarce growth with smooth and thin surface, light orange yellow. Chrome lemon soluble pigment near the growth and coral pink in the medium. Hydrolysis: positive. | Scarce growth, light orange. Hydrolysis of Ca-malate: negative. | Poor growth, light orange. No soluble pigment. Ca-malate digestion: negative. | Fair growth colorless Whitish pink aerial mycelium. Partial digestion of Ca-malate. |
| Egg albumin agar | Abundant growth with smooth surface, light orange. Light yellow soluble pigment. | Abundant growth with smooth surface, orange. No soluble pigment. | Good growth with smooth surface orange-yellow. Light yellow soluble pigment. | Fair growth, pink. |
| Peptone glucose agar | Abundant growth, slightly wrinkled, deep orange. Pinkish aerial mycelium. Yellow soluble pigment. | Abundant growth, wrinkled, deep orange. Gold yellow soluble pigment. | Abundant growth with wrinkled surface, burnt amber. Burnt amber soluble pigment. | |
| Gelatine Nitrate broth | hydrolysis: positive reduction: negative | hydrolysis: positive reduction: negative | hydrolysis: positive reduction: negative | hydrolysis: positive reduction: negative |
| Litmus milk | no coagulation no peptonization | no coagulation no peptonization | no coagulation no peptonization | no coagulation no peptonization |
| Peptone yeast extract iron agar (Medium n° 6 Shirling and Gottlieb) | Moderate growth with smooth surface, pale orange. $H_2S$ production: negative | Moderate growth with smooth surface, pale orange. $H_2S$ production: negative. | Poor growth with smooth surface, colorless. No soluble pigment. $H_2S$ production: negative. | |
| Potato plug | Scarce growth, orange. | Very scarce growth, orange. | Poor growth, light orange. | Poor growth, colorless. |
| Loeffler blood serum | No growth | No growth | No growth | |
| $H_2O$ + agar Difco 2% | Scarce growth colorless. Traces of white aerial mycelium. Abundant production of spores. | Scarce growth, colorless. Traces of white aerial mycelium. Abundant production of spores. | Scarce growth, colorless Traces of white aerial mycelium. Abundant production of spores. | |
| Skim milk agar | Abundant growth with smooth surface, orange. Cadmium yellow soluble pigment. Hydrolysis of casein: good. | Good growth, slightly wrinkled, orange with brown shadow. Hazel brown soluble pigment. Hydrolysis of casein: good. | Abundant growth with wrinkled surface, orange. Gold brown soluble pigment. Casein hydrolysis: strongly positive. | |

Shirling and Gottlieb: Methods for characterization of Streptomyces species, Intern. J. Syst.Bact., 16,313–338 (1966).

The following table 3 reports the physiological characteristics of the new Nocardia Strains compared with those of the parent strain.

Following Table 4 reports the utilization of carbon sources examined according to the method of Pridham and Gottlieb (J.Bact. 56, 107, 1948).

TABLE 3

| | N.mediterranea (D-2) | N.mediterranea (MM 18-6) | N.mediterranea (M-36) | Streptomyces mediterranei (ME/83) |
| --- | --- | --- | --- | --- |
| Strach hydrolysis | − | − | − | ± |
| Tyrosin hydrolysis | + + | + + + | + + + | − |
| Casein hydrolysis | + + | + + | + + + | |
| Ca-malate hydrolysis | + + | − | − | + |
| Nitrate reduction | − | − | − | − |
| Litmus milk | no coagulation no peptonization | no coagulation no peptonization | no coagulation no peptonization | no coagulation no peptonization |
| Gelatin liquefaction | + + | + + | + + | + |

TABLE 4

| | N. mediterranea (D-2) | N. mediterranea (MM 18-6) | N. mediterranea (M-36) | Streptomyces mediterranei (ME/83) |
|---|---|---|---|---|
| Arabinose | + | +++ | ++ | +++ |
| Xylose | + | + | ++ | ++ |
| Glucose | ++ | +++ | ++ | ++ |
| Mannose | + | ++ | ++ | ++ |
| Fructose | ++ | +++ | ++ | ++ |
| Lactose | + | +++ | ++ | ++ |
| Sucrose | + | ± | ++ | ++ |
| Inositol | + | + | ++ | ++ |
| Rhamnose | + | + | ++ | ++ |
| Raffinose | − | − | − | − |
| Salicin | ± | + | + | + |
| Mannitol | ++ | +++ | ++ | ++ |
| Glicine | + | ± | + | − |
| Sorbitol | − | − | − | − |
| Ma-succinate | − | − | − | + |
| Na-citrate | − | − | − | − |
| Na-acetate | − | − | − | − |
| Inulin | ± | + | − | − |
| Dulcitol | − | − | − | − |
| Cellulose | − | − | − | − |
| Maltose | ++ | +++ | ++ | + |
| Galactose | + | ++ | ++ | +++ |
| Glicerol | ++ | +++ | ++ | +++ |

FERMENTATION

The procedure for the fermentation essentially consists in cultivating one of said mutants of *Streptomyces mediterranei* in a nutrient medium containing assimilable carbon and nitrogen sources and essential mineral salts, until a substantial antibiotic activity is imparted to said medium and in extracting the rifamycins from the medium. More particularly these mutants are cultivated under stirred and aerated submerged conditions at a temperature ranging from 25° to 37° C., and preferably at 28° C. As the sources of carbon the following carbohydrates and carbon derivatives can be used: glucose, galactose, lactose, sucrose, maltose, glycerol, mannitol, etc. Useful nitrogen sources are for instance aminoacids and their mixtures, peptides, proteins and their hydrolisates, as peptone, yeast extract, soybean meal, corn steep liquor, fish soluble, meet extracts, aqueous fractions from cereal seeds. The fermentation can be carried out for 180–220 hours. The starting pH, generally adjusted at about 6.4–6.6 increases at the end of the fermentation to 7.0–8.5. Generally the best results are observed at the 200 hours of the fermentation. At the end of the fermentation the rifamycins can be isolated by the following procedure. The fermentation medium is filtered at the final pH of 7.0–8.5. The filtrate is quickly acidified, preferably to a pH lower than about 5, to ensure the best stability to the antibiotic substance. The activity is extracted with water immiscible solvents such as chloroform, butanol, ethyl, propyl, butyl or amyl acetate. The ratio between the volume of the medium and that of the solvent changes dependently on the choosen solvent: generally a ratio ranging from 2:1 to 10:1 is used.

The mycelium still retains a microbiological activity, which is extracted from the mycelium by means of a water immiscible solvent, and then combined with the organic phase, already containing most of the rifamycins. Alternatively, the extraction of the activity from the mycelium can be effected by means of a solvent miscible with water such as acetone. In this case, the liquid is filtered, the acetone is evaporated in vacuo, the rifamycins are extracted with a water immiscible solvent and the procedure is carried on as said above.

Once most of the antibiotic activity has been transferred into the solvent, this is distilled in vacuo to dryness, preferably at a temperature lower than 30° C.

PURIFICATION

The crude extract of rifamycins can be purified chromatographically on a column of silica-gel. Prior to chromatography it is convenient to dissolve the crude extract in a phosphate buffer pH 7.0–8.0 and to treat with a mild oxidizing agent. The buffer solution is then extracted with a water-immiscible solvent, this organic extract contains a new rifamycin denominated rifamycin P. The extracted buffer solution is acidified to pH 2–4 and then again extracted with a water immiscible solvent. This organic extract contains three new compounds of the rifamycin family denominated rifamycin P, Q and U.

The further purification of rifamycin R is effected by chromatography on a column of suitable adsorbing material such as silica-gel and eluting with an appropriate mixture of organic solvents.

The second organic extract containing rifamycins P, Q and U is purified in a similar way to that described for rifamycin R.

The following examples are given for the purpose of better illutrating the subject of the invention.

EXAMPLE 1

The mutant strains identified as *Nocardia mediterranea* ATCC 31064 is propagated for 6–8 days on Bennett's agar and incubated at 28° C.

With the culture obtained from the agar slant, two 500 ml. Erlenmeyer flasks are inoculated under sterile conditions. The flasks contain 100 ml. of the vegetative medium of the following composition:

| Beef extract | 5 | g. |
|---|---|---|
| Yeast extract | 5 | g. |
| Peptone | 5 | g. |
| Casein hydrolyzate | 3 | g. |
| Glucose | 20 | g. |

The pH is adjusted to 7.3 with NaOH.

The flasks so inoculated are placed on an alternative shaker at 28° C. for 72 hours. The content of the two Erlenmeyer flasks is used as inoculum by pouring it in a 10 liters prefermenter, containing 4 liters of the above mentioned vegetative medium. The incubation is carried out at 28° C. with an agitation of 300 r.p.m. and 1 v/v/m aeration. After 48 hours of growth a volume of 7–10% of packed cells is obtained. In the next stage a 10 liter glass fermenter containing 4 liters of the hereinafter mentioned fermentation medium is used:

|  |  |  |
|---|---|---|
| Peanut flour | 25 | g. |
| Soybean flour | 5 | g. |
| $(NH_4)_2SO_4$ | 9.5 | g. |
| $MgSO_4 \cdot 7H_2O$ | 0.85 | g. |
| Glucose | 95 | g. |
| Glycerol | 40 | g. |
| $KH_2PO_4$ | 1 | g. |
| Propylene glycol | 5 | g. |
| $CaCO_3$ | 8.5 | g. |
| Na diethylbarbiturate | 1.7 | g. |
| $CuSO_4 \cdot 5H_2O$ | 2.8 | mg. |
| $FeSO_4 \cdot 7H_2O$ | 8.5 | mg. |
| $ZnSO_4 \cdot 7H_2O$ | 42.5 | mg. |
| $MnSO_4 \cdot 4H_2O$ | 3.4 | mg. |
| $CaCl_2 \cdot 6H_2O$ | 1.7 | mg. |
| $(NH_4)_6Mo_7O_{24} \cdot 4H_2O$ | 0.85 | mg. |
| $H_2O$ to | 1 | liter |

The pH is adjusted to 7.8 with NaOH. Sterilization for 60 minutes at 120° C. After sterilization the pH is 6.4. An amount of the prefermenter content equal to 5% of the fermenter content is used as inoculum.

The fermentation is carried out at 28° C. with a 750 r.p.m. agitation and aerating at a rate of 1 v/v/m. Silicone A is used as antifoam. The culture broth turns to a characteristic red-brown color during the fermentation. After 200 hours of growth a volume of packed cells is obtained. The pH of the broth is 7.5 and at this moment the broth is harvested.

EXAMPLE 2

A culture of *Nocardia mediterranea* ATCC 31064 obtained as disclosed in example 1, is prepared in a flask, under stirring, as described in example 1. For the preculture it is poured into a 10 liters glass fermenter, containing 4 liters of the following medium:

|  |  |  |
|---|---|---|
| Glucose | 5 | g. |
| Peanut flour | 7.5 | g. |
| $CaCO_3$ | 1.65 | g. |
| $MgSO_4 \cdot 7H_2O$ | 0.33 | g. |
| $KH_2PO_4$ | 0.33 | g. |
| $FeSO_4 \cdot 7H_2O$ | 3.3 | mg. |
| $ZnSO_4 \cdot 7H_2O$ | 16.5 | mg. |
| $MnSO_4 \cdot 4H_2O$ | 1.3 | mg. |
| $H_2O$ to | 1 | liter |

The pH is adjusted to 7.5. Sterilization 50 minutes at 120° C. After sterilization the pH value is 6.4. After 48 hours of growth the volume of packed cells is 6–8% of total volume. An inoculum equal to 10% is used for a 20 liters glass fermenter, containing 10 liters of the following fermentation medium:

|  |  |  |
|---|---|---|
| Corn steep liquor | 20 | g. |
| Soybean flour | 15 | g. |
| $(NH_4)_2SO_4$ | 6 | g. |
| $MgSO_4 \cdot 7H_2O$ | 0.85 | g. |
| Glucose | 100 | g. |
| $KH_2PO_4$ | 1 | g. |
| $CaCO_3$ | 6 | g. |
| $FeSO_4 \cdot 7H_2O$ | 8.5 | mg. |
| $ZnSO_4 \cdot 7H_2O$ | 42.5 | mg. |
| $MnSO_4 \cdot 4H_2O$ | 3.4 | mg. |
| $CuSO_4 \cdot 5H_2O$ | 2.8 | mg. |
| $CoCl_2 \cdot 6H_2O$ | 1.7 | mg. |
| $H_2O$ to | 1 | liter |

The pH is adjusted to 7.8 with NaOH. Sterilization for 50 minutes at 120° C. After sterilization the pH is 6.4. The fermentation is carried out at 28° C. for 200 hours. The pH of the fermentation broth at the harvest is 7.5.

The fermentation broths obtained in examples 1 and 2 are purified in the following way. The mycelium is removed by filtration and discarded, the filtrate is adjusted to pH 2.0 with 10% (v/v) hydrochloric acid and extracted three times with an equal volume of ethyl acetate. This organic extract is concentrated to dryness under vacuum at 35° C. and the residue (4 g. from example 1 and 11 g. from example 2) is dissolved in 0.05 M sodium phosphate buffer pH 7.5 and sodium nitrite added to give a final concentration of 0.2% (w/v). After stirring for 30 min. at room temperature the buffer solution is extracted three times with an equal volume of ethyl acetate. The combined organic extracts are concentrated to dryness under vacuum at 35° C. ($1^{st}$ ethyl acetate extract). The exhausted buffer solution is adjusted to pH 2.0 with 10% hydrochloric acid and extracted with an equal volume of ethyl acetate three times. The combined organic extracts are concentrated to dryness under vacuum at 35° C. ($2^{nd}$ ethyl acetate extract).

The dry powder from the $1^{st}$ ethyl acetate extract (1.4 g example 1 and 4.2 g. example 2) is dissolved in chloroform and chromatographed on a column of silica-gel (70–230 Mesh ASTM) using chloroform containing 2% (v/v) methyl alcohol as an eluent. Rifamycin R is the first major product to elute from the column recognizable by its orange-brown colour.

On thin layer chromatography using silica-gel plates (merck 60 $F_{254}$) with chloroform: methyl alcohol as solvent system (95:5) rifamycin R has an Rf of 0.59. The fractions containing rifamycin R are combined, taken to dryness under vacuum at 35° C., redissolved in ethyl acetate which is then washed with 0.01 N hydrochloric acid and finally with water. The organic extract is concentrated to a small volume and rifamycin R crystallizes from solution at 4° C. (obtained 600 mg. from example 1 and 1.6 g. from example 2). The second ethyl acetate extract is purified by column chromatography on silica-gel in a similar way to rifamycin R. The dry residue (2.4 g. from example 1 and 4.2 g. from example 2) is dissolved in chloroform and applied to the silica gel.

The column is eluted with a mixture of chloroform and methyl alcohol (98:2). The first compound to emerge is rifamycin U, then rifamycin P and finally rifamycin Q. All three of these compounds have a yellow orange colour in the eluent solution and can be identified on the bases of their mobility on thin layer chromatography. On silica gel plates (Merck 60 $F_{254}$) using chloroform: methanol (95:5) as solvent system, the Rf values are the following:

| | | |
|---|---|---|
| rifamycin U | Rf = 0.63 | |
| rifamycin P | Rf = 0.57 | |
| rifamycin Q | Rf = 0.32 | |

The appropriate fractions containing rifamycins U, P and Q are combined taken to dryness under vacuum and crystallized from ethyl acetate. From the first example are obtained rifamycin U 80 mg., rifamycin P 400 mg., rifamycin Q 280 mg: from the second example rifamycin U 190 mg., rifamycin P 900 mg., rifamycin Q 750 mg.

By following essentially the same procedure of the above examples but using respectively *Nocardia mediterranea* ATCC 31065 or *Nocardia mediterranea* ATCC 31066 as the producing strains, yields of the same order as above are obtained.

PHYSICO-CHEMICAL CHARACTERISTICS OF THE NOVEL RIFAMYCINS

Rifamycin P (1) Elemental analysis (%): Found, C=60.6; H=6.2; N=3.8; O=25.2; S=4.1.

(2) U.V. and visible absorption bands:
The compound shows the following values:

| methanol | | 0.1 N HCl | |
|---|---|---|---|
| $\lambda_{max}(m\mu)$ | $E_1^{1\%}$ cm | $\lambda_{max}(m\mu)$ | $E_1^{1\%}$ cm |
| 406 | 197 | 416 | 183 |
| 350 | (shoulder) | 300 | 319 |
| 297 | 344 | 225 | 521 |
| 257 | 423 | | |
| 224 | 550 | | |

The complete figure of the spectrum is given in FIG. 1. The spectrum was recorded with Perkin Elmer Spectracord 4000 A instrument.

(3) Infrared Spectrum: The most significant absorption peaks in Nujol occur at the following frequencies (cm$^{-1}$): 3700–3150 (m,br); 3100 (w); 3060–2800 (vs); 1465 (s); 1380 (b): Nujol; 1722 (m); 1645 (m,br); 1580 (m); 1510 (m); 1325 (m); 1250 (s br); 1160 (m); 1130 (w); 1070 (m, br) 1030 (w); 982 (m); 960 (m); 925 (w); 890 (m); 818 (w); 770 (w); 735 (w).

A complete figure of the I.R. spectrum is given in FIG. 2. The spectrum was recorded with a Perkin Elmer Mod. 421 instrument.

(4) Mass spectrum: The mass spectrum obtained at 70 eV shows the molecular ion peak M+ at the following m/e value: 738. The spectrum was recorded with an Hitachi Perkin Elmer RMU-6L instrument.

(5) Nuclear Magentic Resonance spectrum: The complete figure of N.M.R. spectrum at 100 MH$_z$ in CDCl$_3$ is given in FIG. 3. This compound does not show the characteristic polarographic behavior of the rifamycins possessing a chromophoric moiety with quinonic structure.

Rifamycin O (1) Elemental analysis: Found, C=60.7; H=6.3; N=3.60; O=25.3; S=4.2

(2) U.V. and visible absorption bands:
The compound shows the following values in methanol:

| $\lambda_{max}(m\mu)$ | $E_1^{1\%}$ cm |
|---|---|
| 406 | 178 |
| 350 | (shoulder) |
| 297 | 305 |
| 257 | 405 |
| 224 | 518 |

(3) Infrared Spectrum: The most significant absorption peaks in Nujol occur at the following frequencies (cm$^{-1}$): 3700–3300 (s,br); 3300–3080 (m br); 3040–2780 (vs); 1460 (s); 1378 (s): Nujol; 1740 (m); 1700 (m); 1650 (s, br); 1605 (s, br); 1555 (s); 1510 (m, br); 1315 (w); 1275 (m); 1240 (m); 1220 (m); 1160 (m); 1090 (m); 1050 (m,br); 1020 (w); 970 (m); 945 (w); 910 (m); 808 (m); 765 (w); 720 (w).

A complete figure of the I.R. spectrum is given in FIG. 4.

(4) Nuclear Magnetic Resonance Spectrum: The complete figure of the N.M.R. spectrum at 60 MH$_z$ in CDCl$_3$ is given in FIG. 7.

Rifamycin R (1) Elemental analysis: Found: C=62.0; H=6.4; N=2.2; O=29.6.

(2) U.V. and visible absorption bands:
The compound shows the following values in which 0.1 N HCl in methanol:

| $\lambda_{max}(m\mu)$ | $E_1^{1\%}$ cm |
|---|---|
| 219 | 444 |
| 281 | 415 |
| 340 | 114 |
| 410 | 72 |

(3) Infrared Spectrum: The most significant absorption peaks in Nujol occur at the following frequencies (cm$^{-1}$): 3700–3100 (s br); 3040–2780 (vs); 1465 (s); 1380 (s): Nujol; 1745 (s); 1710 (m); 1640 (s); 1600 (s); 1505 (s); 1415 (m); 1325 (s); 1260 (s, br); 1220–1130 (s, br); 1120 (w); 1075 (s); 1020 (w); 975 (s); 950 (w); 920 (w); 888 (m); 823 (m); 785 (w, br); 735 (w, br); 650 (w, br).

A complete figure of the I.R. spectrum is given in FIG. 5.

(4) Mass spectrum: The mass spectrum obtained at 70 eV shows the molecular ion peak M+ at the following m/e value: 711.

(5) Nuclear Magnetic Resonance spectrum: The complete figure of the N.M.R. spectrum at 60 MH$_z$ in CDCl$_3$ is given in FIG. 6.

The compound shows the characteristic polorographic behavior of the rifamycins possessing a chromophoric moiety with quinonic structure.

The above data support the following structure for rifamycin R.

Rifamycin U (1) U.V. and visible absorption bands:
The compound shows the following values in methanol:

| $\lambda_{max}$ (m$\mu$) | $E_1^{1\%}$ cm |
|---|---|
| 412 | 163 |
| 353 | (shoulder) |
| 299 | 265 |
| 258 | 389 |
| 220 | 451 |

(2) Infrared spectrum: The most significant absorption peaks in Nujol occur the following frequencies (cm$^{-1}$): 3700–3100 (m,br); 3060 (vw); 3040–2740 (vs), 2720 (vw), 1460 (s), 1378 (m): Nujol; 1750–1705 (m,br); 1680–1620 (m,br); 1600 (s); 1558 (s); 1490 (w, shoulder); 1308 (w); 1270 (w, shoulder); 1245 (m, shoulder); 1225 (m); 1160 (m); 1120 (w); 1090 (vw); 1070 (w); 1030 (vw); 1020 (vw); 1000 (vw); 975 (w); 960 (w, shoulder); 905 (m); 850 (m); 802 (w); 800 (vw, shoulder); 777 (vw); 760 (vw); 720 (vw); 685 (vw); 670 (vw).

BIOLOGICAL ACTIVITY OF THE COMPOUNDS

The in vitro activity spectrum of rifamycins P, Q and R is reported in the following table:

| Strains | Minimal inhibition concentration ($\mu$g/ml) | | | |
|---|---|---|---|---|
| | Rifamycin P | Rifamycin Q | Rifamycin R | Rifamycin M |
| Staphylococcus aureus ATCC 6538 | 0.00235 | 0.039 | 0.019 | 0.05–0.1 |
| Staphylococcus aureus ATCC 6538 (20% bovine serum) | 0.00235 | 0.078 | 0.0047 | — |
| Staphylococcus aureus Tour | 0.0035 | 0.06 | 0.00235 | — |
| Staphylococcus aureus Tour rifampicin-resistant | 25–50 | >100 | 100 | — |
| Streptococcus hemolyticus C 203 | 0.0047 | 0.019 | 0.00312 | — |
| Streptococcus faecalis ATCC 10541 | 0.0035 | 0.312 | 0.19 | — |
| Diplococcus pneumoniae UC 41 | 0.0047 | 0.039 | 0.00625 | — |
| Proteus vulgaris X 19 N ATCC 881 | 0.78 | 12.5 | 12.5 | — |
| Escherichia coli ATCC 10536 | 3.12 | 12.5 | 50 | >50 |
| Klebsiella pneumoniae ATCC 10031 | 12.5 | 50 | — | — |
| Pseudomonas aeruginosa ATCC 10145 | 12.5 | 50 | 100 | — |
| Mycobacterium tub. H37Rv ATCC 9360 | 1 | 2.5 | 0.1 | 2.5 |

—: Activity not determined

The novel compounds are active also in the laboratory animals injected with Staphylococcus aureus, Escherichia coli. The following table reports the results of representative experiments on mice in comparison with a known natural rifamycin, i.e. rifamycin SV.

| Compound | Infecting Strain | ED$_{50}$mg/kg. | |
|---|---|---|---|
| | | s.c. | o.s. |
| rifamycin P | Staphylococcus aureus | 0.3 | 0.8 |
| rifamycin P | Escherichia coli | 40 | — |
| rifamycin Q | Staphylococcus aureus | 8 | — |
| rifamycin SV | Staphylococcus aureus | 17 | 74 |

Rifamycin P which results to be the most active natural rifamycin so far isolated has also low toxicity since its LD$_{50}$ value in mice is higher than 500 mg/kg. i.p.

We claim:

1. A biologically pure culture of the microorgansim Nocardia mediterranea, having the identifying characteristics of ATCC 31064, said culture being capable of producing an antibiotic selected from the group consisting of rifamycin P, Q, R, and U in a recoverable quantity upon aerobic fermentation in an aqueous nutrient medium containing assimilable sources of carbon, nitrogen, and inorganic minerals.

2. A biologically pure culture of the microorganism Nocardia mediterranea, having the identifying characteristics of ATCC 31065, said culture being capable of producing an antibiotic selected from the group consisting of rifamycin P, Q, R, and U in a recoverable quantity upon aerobic fermentation in an aqueous nutrient medium containing assimilable sources of carbon, nitrogen, and inorganic minerals.

3. A biologically pure culture of the microorganism Nocardia mediterranea, having the identifying characteristics of ATCC 31066, said culture being capable of producing an antibiotic selected from the group consisting of rifamycin P, Q, R, and U in a recoverable quantity upon aerobic fermentation in an aqueous nutrient medium containing assimilable sources of carbon, nitrogen, and inorganic minerals.

4. A rifamycin compound defined as rifamycin R having the following formula:

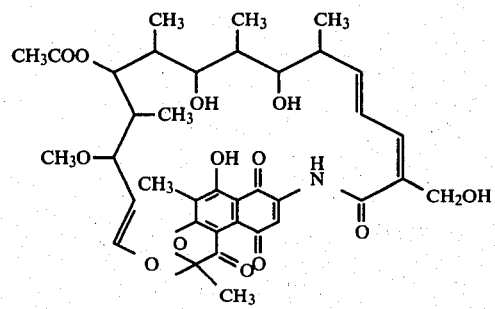

* * * * *

UNITED STATES PATENT AND TRADEMARK OFFICE
CERTIFICATE OF CORRECTION

PATENT NO. : 4,263,404
DATED : April 21, 1981
INVENTOR(S) : Richard J. White, et al.

It is certified that error appears in the above-identified patent and that said Letters Patent are hereby corrected as shown below:

Column 2, Table 1, under subtitle Spores, under second Cylindrical, should read —(0.8-1 µm x 3.0-5.0µ)—.

Column 11, line 59, Rifamycin O, should read —Rifamycin Q—.

Column 13 and 14, Table, last column, "Rifamycin M" should read —Rifamycin U—.

Signed and Sealed this

Twenty-fourth Day of November 1981

[SEAL]

Attest:

Attesting Officer

GERALD J. MOSSINGHOFF

Commissioner of Patents and Trademarks